United States Patent [19]

Keeler

[11] Patent Number: 4,888,744

[45] Date of Patent: Dec. 19, 1989

[54] PULSED DIRECTIONAL DOPPLER FREQUENCY DOMAIN OUTPUT CIRCUIT

[75] Inventor: John H. Keeler, North Haven, Conn.

[73] Assignee: American Home Products, New York, N.Y.

[21] Appl. No.: 271,743

[22] Filed: Nov. 15, 1988

[51] Int. Cl.[4] .............................................. G01S 15/02
[52] U.S. Cl. ........................................ 367/90; 367/87
[58] Field of Search ............................. 367/90, 91, 87; 342/104, 105; 128/661.07, 661.09, 662.01; 364/413.07; 73/627

[56] References Cited

U.S. PATENT DOCUMENTS 3,233,212 2/1966 Auer, Jr. et al. ..................... 367/90

Primary Examiner—Thomas H. Tarcza
Assistant Examiner—Daniel T. Pihulic
Attorney, Agent, or Firm—Darby & Darby

[57] ABSTRACT

An electrical circuit to detect frequency domain information from ultrasonic signals that have been doppler shifted by motion of an object in the field of the ultrasonic beam. The circuit receives the doppler shifted signal, creates separate upper and lower sideband signals and compares the signals to a threshold level to produce digital transition pulses. The transmitter pulses are digitized to form pulses of uniform width and amplitude, whose frequency can be correlated to the object motion.

8 Claims, 2 Drawing Sheets

IN₁

IN₂

THRESHOLD 70  72

COMPARATOR #1 OUT

MONOSTABLE #1 OUT (Q)

COMPARATOR #2 OUT

MONOSTABLE #2 OUT ($\overline{Q}$)

ANALOG OUTPUT

PULSED DIRECTIONAL DOPPLER FREQUENCY DOMAIN OUTPUT CIRCUIT

BACKGROUND OF THE INVENTION

This invention relates to electrical circuits which produce signals representative of the motion of an object under examination, and more particularly, to electrical circuits useful in fetal heart monitors.

It is known that the motion of an object can be determined by creating a beam of ultrasonic energy with an ultrasonic generator, or transducer, directing the beam at the object, and measuring the doppler shift in the ultrasonic signal reflected from the object and picked up by the transducer. Electrical circuits are used to analyze the received signal to determine the doppler shift caused by the motion of the object in the field of the transmitted ultrasonic beam. The signals from the circuit are useful in determining the rate, velocity and direction of motion of an object, e.g. a fetal heart. With respect to a fetal heart, the signals are particularly useful in the determination of heart rates and related information.

In practice a reflected, doppler-shifted signal is applied to the circuit. This signal has information that is proportional to the velocity of the motion of the heart in the path of the transmitted ultrasonic beam. In particular, the input signal has an upper sideband that is produced by motion of the fetal heart under study toward the receiving transducer, and a lower sideband produced by motion of the heart away from the transducer. The amplitude of the upper and lower sideband ultrasonic signals received by the transducer and created by the doppler effect, relate to the direction and speed of motion of the heart.

The electrical circuitry separates the upper and lower sidebands of the doppler-shifted ultrasound signal into two signals that correspond to motion toward and away from the transducer. The amplitudes of these signals are processed and utilized to analyze the fetal heart rate and condition.

Although in the prior art circuits, the amplitudes of the received ultrasonic signals are analyzed, there is also information contained in the frequency change of the ultrasonic doppler shifted signal. Thus, it would be advantageous, and an improvement over prior art electrical circuitry devices, to have a circuit which detects frequency domain information from the ultrasonic signals that have been doppler shifted by motion in the field of the ultrasonic beam.

SUMMARY OF THE INVENTION

The present invention is directed to providing an electrical circuit to detect frequency domain information from the ultrasonic signals that have been doppler shifted by motion in the field of the ultrasonic beam, which information is then useful in determining the direction of motion of the heart and other heart-related information.

In an illustrative embodiment of the invention, the doppler shifted ultrasonic signal has the upper and lower sidebands of the input signal separated. These two signals are then rectified and compared to a threshold which is set slightly above the noise level. The two output signals from the comparator are square-wave signals which follow the frequency of the doppler shifted signal and are independent of the amplitude.

Each square-wave signal is routed to a monostable multivibrator, which produces a pulse of predetermined duration on each transition. The output signal of each monostable is thus a train of constant width pulses. The average energy of this train of pulses is proportional to the frequency of the input to the monostable.

To obtain the average values of the outputs of the monostable, the outputs are applied to an integrator. The integrator output is pulled in one direction for motion toward the transducer and the other direction for motion away from the transducer.

As an alternative, instead of converting the monostable pulses to an analog signal in the integrator, these digital pulses may be used directly in an autocorrelator to obtain the frequency change information. Also, phase-locked loops or frequency-to-voltage circuits can be used to obtain the frequency domain information.

BRIEF DESCRIPTION OF THE DRAWINGS

The foregoing and other features of the present invention will be more readily apparent from the following detailed description and drawings of an illustrative emodiment of the present invention wherein.

DESCRIPTION OF ILLUSTRATIVE EMBODIMENTS

According to the present invention, a fetal monitor probe 10 is located on the abdomen of a pregnant woman. This probe includes an ultrasonic transducer which creates an ultrasonic signal that is transmitted through the woman's abdomen to her uterus. The signal passes through the wall of the uterus and the amniotic fluid into the fetus. Part of the ultrasonic signal is reflected back to the probe as it passes through each body structure (shown in dotted line). However, if the body structure moves, the reflected signal has a doppler frequency shift which gives the signal an amplitude and frequency variation from the transmitted signal.

The probe my be equipped with a second transducer which receives the reflected ultrasonic signal and converts it into an electrical signal. Alternatively, the transducer 10 may act as a receiver when it is not transmitting.

The heartbeat of the fetus creates a signal with a doppler shift. In particular, the probe is positioned so that as the heart beats, it moves toward and away from the probe. As it moves toward the probe, the reflected frequency is increased, thus creating an upper sideband. As the heart moves away from the probe, the reflected frequency is decreased and a lower sideband is created.

The received ultrasonic signal is passed through a product detector 12 so that the upper and lower sidebands are separated. These two signals may then be separately rectified in circuits 14 to form signals $IN_1$ and $IN_2$, respectively. The rectification gives the signals a single polarity. If the signals are full wave rectified, instead of merely being half wave rectified, the resulting signal has twice the frequency and hence yields twice the resolution. Either method of rectification is contemplated by the present invention.

Figure 1:
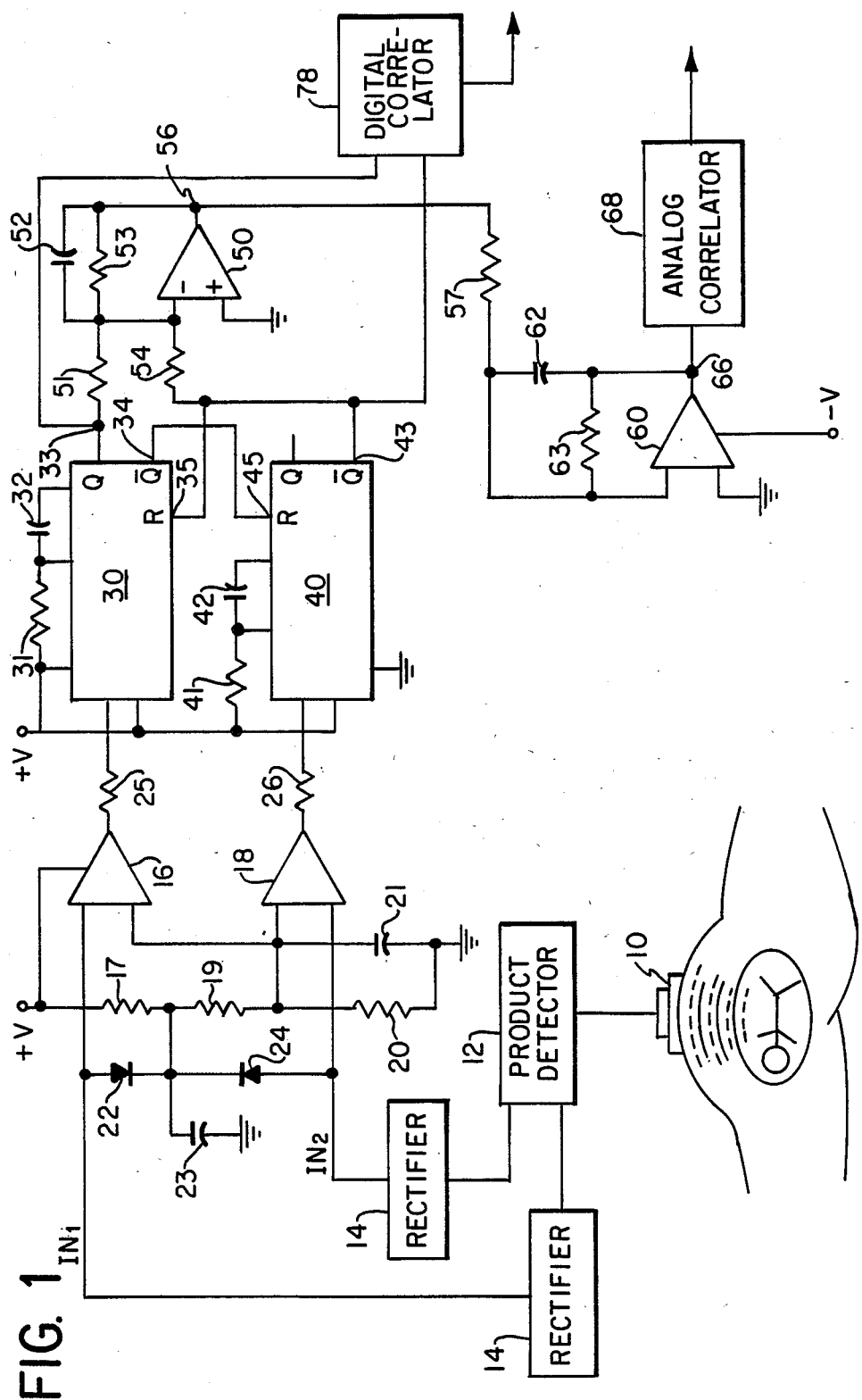
FIG. 1 is a schematic of an electrical circuit according to the present invention.
Figure 2A:
FIG. 2 shows a timing diagram of the input and output signals of several of the electrical components shown in FIG. 1, as well as the input signals to the electrical circuit of the present invention.

According to the present invention, and as shown in FIG. 1, the upper sideband signal $IN_1$ is applied to comparator 16, where it is compared to a threshold voltage level created by resistors 17, 19 and 20, and capacitor 21. As shown in FIG. 2a, this doppler shifted signal varies in both amplitude and frequency. In prior art arrangements, the amplitude variation was detected and used to monitor fetal heart rate and other parameters. However, according to the present invention, only the change in frequency is monitored.

Figure 2B:
Figure 2C:
Figure 2D:
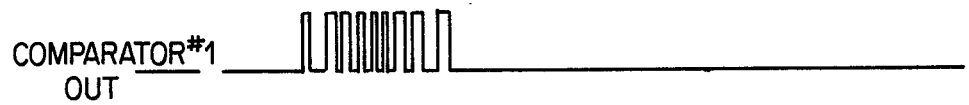

Whenever the input $IN_1$ is more positive than the threshold, the output of the comparator 16 is high as shown in FIG. 2d. A series of high amplitude signals cause capacitor 23 to be charged through diode 22. This raises the voltage at the junction of resistors 17 and 19, and charges capacitor 21 to a more positive voltage, raising the threshold and improving noise immunity. The first positive excursion 70 in FIG. 2c corresponds to this change in the threshold. For low amplitude signals, resistor 20 keeps the threshold at a fixed value set by the ratio of resistors 17, 19 and 20, which in practice is about 0.8 volts.

Figure 2E:
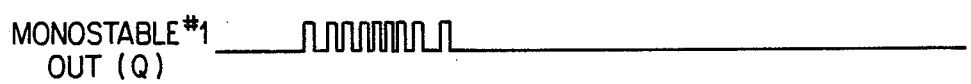
Figure 2F:
Figure 2G:

The output of comparator 16 is applied through resistor 25 to the input of monostable multivibrator 30. Resistor 25, along with the internal protection diodes in monostable 30, level shift the comparator output from plus or minus 15 volts to plus 5 volts and ground. The positive edge of the output of comparator 16 triggers monostable 30, causing fixed-time output pulses as shown in FIG. 2e, whose width is determined by resistor 31 and capacitor 32. Output 33 of monostable 30 is positive when it is triggered.

An amplifier 50 is connected as an integrator, with resistor 51 connecting the output of monostable 30 to its inverting input and capacitor 52 connected from its output to its input. Amplifier 50 integrates the output of monostable 30. During the time that the output of monostable 30 is high, the output of amplifier 50 is driven negative. Thus, the period during which the output of monostable 30 is high determines the negative amplitude of the output of amplifier 50. When monostable 30 is not triggered, resistor 53 which is connected between the output and inverting input of amplifier 50, removes the charge from capacitor 52 and returns the output of amplifier 50 toward negative 2.81 volts. As a result, When the frequency is increasing during the beginning of the doppler shifted signal, an increasingly negative signal is created. As this frequency decreases near the end of the signal, the signal returns to a more positive level.

The lower sideband signal $IN_2$(FIG. 2b) is applied to a comparator 18, where it is compared to the same threshold as the input $IN_1$. High amplitude signals for $IN_2$ also charge capacitor 23 through diode 24 to increase the threshold. This is represented by the second positive excursion 72 in the threshold signal (FIG. 2c). The output of comparator 18 triggers a monostable 40 through resistor 26, causing a fixed-time output pulse as determined by resistor 41 and capacitor 42. Thus, the operation of monostable 40 is identical to the operation of monostable 30.

The output 43 of monostable 40 is taken from its complimentary output $\overline{Q}$ and is applied to the inverting input of amplifier 50 through resistor 54. Consequently, the untriggered output is at +5 volts and the triggered output at 0 volts. Resistor 54 and capacitor 52 integrate the pulses, driving the output of integrator 50 in the positive direction. This is the opposite of the effect of the output of monostable 30, causing amplifier 50 to act as a difference amplifier as well as an integrator.

Figure 2H:

The output 56 of amplifier 50 is connected to amplifier 60 through a resistor 57. Amplifier 60 inverts the output of amplifier 50, level-shifts the output to a nominal level, e.g. a +1 volt level, and filters the signal to smooth the integrator output. The resulting signal at output 66 of amplifier 60 is shown in FIG. 2h. Capacitor 62 and resistors 57, 63 act as the filter. The ratio of the values of resistor 63 to resistor 57 sets the gain of the output of amplifier 60, e.g. such that the nominal −2.81 volts at the output of amplifier 50 is +1 volt.

The input $IN_1$ drives the output of amplifier 60 more positive than the nominal level, while the input at $IN_2$ drives it more negative. This results in a single waveform as shown at FIG. 2h. In a preferred embodiment, the signal has a range between 0 and +2 volts. These levels were chosen for optimum compatibility with the input of a conventional analog correlator 68 utilized to derive heart rate and other information from the signal.

An additional feature of the circuit shown in FIG. 1 is the cross-coupling of the reset inputs of monostables 30 and 40. When monostable 30 is triggered, the $\overline{Q}$ output 34 goes low, holding the reset input 45 of monostable 40 to a low level. This keeps monostable 40 from being triggered during the time monostable 30 is active, which gives the circuit additional noise immunity. Similarly, the $\overline{Q}$ output 43 of monostable 40 is connected to the reset input 35 of monostable 30.

In an alternative embodiment of the present invention, a digital correlator 78 can be used instead of an analog correlator. In such a case, amplifiers 50 and 60 shown in FIG. 1 would be unnecessary. Instead, the digital outputs from terminals 33 and 43 of monostables 30 and 40, respectively, would be the circuit outputs. These outputs of monostables 30 and 40 and would be directly processed as digital signals, without the need for returning them to analog signals (e.g. in amplifiers 50 and 60) and then turning them back into digital signals. Thus, where the correlator inputs can be digital, simpler circuitry, greater accuracy and much faster correlation is obtained.

While the invention has been particularly shown and described with reference to preferred embodiments thereof, it will be understood by those skilled in the art that various changes in form and details may be made therein without departing from the spirit and scope of the invention.

What is claimed is:

1. An apparatus for receiving a doppler shift signal with upper and lower sidebands representative of the motion of an object under examination toward and away from a receiver, respectively, and producing an output indicative of at least the rate of motion, comprising:
   (a) converter means for receiving the doppler shift signal and creating separate upper and lower sideband signals;
   (b) comparator means for separately comparing said upper sideband and said lower sideband signal to a threshold level and producing compared sideband signal outputs at one level whenever the sideband signals exceed the threshold and at a second level when they do not;
   (c) digitizing means for producing an output indicative of at least the rate of motion of the object under examination and for digitizing the compared sideband signals by creating digitized upper and lower sideband signals in the form of pulses of uniform width and amplitude for at least each transition in one direction of each of said compared sideband signal outputs, wherein the digitizing means comprises an upper sideband monostable multivibrator and a lower sideband monostable multivibrator, each triggered by the rising edges of the respective compared sideband signals from said comparator means; and (d) integrator means comprising an operational amplifier, a capacitor connected from the output to its inverting input of the operational amplifier, and wherein the output of the upper sideband monostable and the complimentary output of the lower sideband monostable are connected through separate resistors to the inverting input of the operational amplifier.

2. An apparatus for receiving a doppler shift signal with upper and lower sidebands representative of the motion of an object under examination toward and away from a receiver, respectively, and producing an output indicative of at least the rate of motion, comprising:

(a) converter means for receiving the doppler shift signal and creating separate upper and lower sideband signals;

(b) comparator means for separately comparing said upper sideband and said lower sideband signal to a threshold level and producing compared sideband signal outputs at one level whenever the sideband signals exceed the threshold and at a second level when they do not;

(c) digitizing means for producing an output indicative of at least the rate of motion of the object under examination and for digitizing the compared sideband signals by creating digitized upper and lower sideband signals in the form of pulses of uniform width and amplitude of for at least each transition in one direction of each of said compared sideband signal outputs; and (d) a digital correlator, wherein said digitized upper and lower sideband signals are input to the digital correlator and are processed for correlating said digitized signals to the motion of the object under examination.

3. An apparatus for receiving a doppler shift signal with upper and lower sidebands representative of the motion of an object under examination toward and away from a receiver, respectively, and producing an output indicative of at least the rate of motion, comprising:

(a) converter means for receiving the doppler shift signal and creating separate upper and lower sideband signals;

(b) comparator means for separately comparing said upper sideband and said lower sideband signal to a threshold level and producing compared sideband signal outputs at one level whenever the sideband signals exceed the threshold and at a second level when they do not;

(c) digitizing means for producing an output indicative of at least the rate of motion of the object under examination and for digitizing the compared sideband signals by creating digitized upper and lower sideband signals in the form of pulses of uniform width and amplitude for at least each transition in one direction of each of said compared sideband signal outputs;

(d) integrator means for combining and averaging the digitized upper and lower sideband signal outputs of said digitizer means; and (e) an analog correlator for correlating the combined and averaged signal to the motion of the object under examination.

4. The apparatus as in claim 3 further comprising inverter-level-shift-filter means for inverting, level shifting and filtering the output of the integrator such that said filtered, inverted, level shifted output of the integrator is an analog signal related to the motion of the object under examination.

5. The apparatus as in claim 2 wherein said converter means further includes means for rectifying the doppler shift signal.

6. The apparatus as in claim 2 wherein said converter means further includes means for half-wave rectifying the doppler shift signal.

7. The apparatus as in claim 2 wherein said converter means further includes means for full-wave rectifying the doppler shift signal.

8. An apparatus for receiving a doppler shift signal with upper and lower sidebands representative of the motion of an object under examination toward and away from a receiver, respectively, and producing an output indicative of at least the rate of motion, comprising:

(a) converter means for receiving the doppler shift signal and creating separate upper and lower sideband signals;

(b) comparator means for separately comparing said upper sideband and said lower sideband signal to a threshold level and producing compared sideband signal outputs at one level whenever the sideband signals exceed the threshold and at a second level when they do not;

(c) digitizing means for producing an output indicative of at least the rate of motion of the object under examination and for digitizing the compared sideband signals by creating digitized upper and lower sideband signals in the form of pulses of uniform width and amplitude for at least each transition in one direction of each of said compared sideband signal outputs, wherein the digitizing means comprises an upper sideband monostable multivibrator and a lower sideband monostable multivibrator, each triggered by the rising edges of the respective compared sideband signals from said comparator means; and (d) means for cross-coupling of the reset inputs of one monostable with the complimentary outputs of the other so as to prevent the simultaneous operation of both monostables.

* * * * *